United States Patent
Johansen et al.

(10) Patent No.: US 8,865,768 B2
(45) Date of Patent: *Oct. 21, 2014

(54) USE OF POLYUNSATURATED KETONES FOR THE TREATMENT OF PSORIASIS

(71) Applicant: Avexxin AS, Trondheim (NO)

(72) Inventors: Berit Johansen, Trondheim (NO); Marit Anthonsen, Trondheim (NO); Wenche Sjursen, Trondheim (NO); Anne K. Holmeide, Oslo (NO); Lars Skattebol, Oslo (NO)

(73) Assignee: Avexxin AS, Trondheim (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/957,899

(22) Filed: Aug. 2, 2013

(65) Prior Publication Data

US 2013/0324613 A1 Dec. 5, 2013

Related U.S. Application Data (63) Continuation of application No. 12/713,917, filed on Feb. 26, 2010, now Pat. No. 8,524,776, which is a continuation of application No. 10/502,414, filed as application No. PCT/GB03/00364 on Jan. 29, 2003, now Pat. No. 7,687,543.

(30) Foreign Application Priority Data

Jan. 29, 2002 (GB) .................................. 0202002.2

(51) Int. Cl.
*A01N 37/00* (2006.01)
*A61K 31/121* (2006.01)
*A61K 31/045* (2006.01)
*A61K 31/557* (2006.01)

(52) U.S. Cl.
CPC ............. *A61K 31/121* (2013.01); *A61K 31/045* (2013.01); *A61K 31/557* (2013.01)
USPC ......................................................... 514/560

(58) Field of Classification Search
None
See application file for complete search history.

(56) References Cited

U.S. PATENT DOCUMENTS

| | | | |
|---|---|---|---|
| 6,255,496 B1 | 7/2001 | Banville et al. | |
| 6,688,468 B2 | 2/2004 | Waterman | |
| 2006/0162240 A1 | 7/2006 | Filippini et al. | |

FOREIGN PATENT DOCUMENTS

| | | |
|---|---|---|
| JP | 09268153 A | 10/1997 |
| JP | 11199493 | 7/1999 |

(Continued)

OTHER PUBLICATIONS

Atsumi et al., "Distinct Roles of Two Intracellular Phospholipase A2s in Fatty Acid Release in the Cell Death Pathway," Journal of Biological Chemistry (2000), 275(24):18248-18258.

(Continued)

*Primary Examiner* — Paul Dickinson
(74) *Attorney, Agent, or Firm* — Edwards Wildman Palmer LLP; Peter F. Corless; Christopher R. Cowles (57) ABSTRACT

Psoriasis is a common, chronic, inflammatory skin disorder. This invention provides the use of a compound of formula (I) R—CO—X (Wherein R is a $C_{16-24}$ unsaturated hydrocarbon group optionally interrupted by $\alpha$, $\beta$, $\gamma$, or $\delta$ to the carbonyl group by a heteroatom or group of heteroatoms selected from S, O, N, SO, $SO_2$ said hydrocarbon group comprising at least 5 non-conjugated double bonds; and X is an electron withdrawing group) in the manufacture of a medicament for the treatment of psoriasis.

6 Claims, 4 Drawing Sheets

(56) References Cited

FOREIGN PATENT DOCUMENTS

| WO | 0002561 A1 | 1/2000 |
|----|------------|--------|
| WO | 02060535 A1 | 8/2002 |

OTHER PUBLICATIONS

Brown et al., "Protection of Oxygen-Sensitive Pharmaceuticals with Nitrogen", Journal of Pharmaceutical Sciences, vol. 58, No. 2, pp. 242-245 (1969).

Holmeide et al., "Syntheses of some polyunsaturated trifluoromethyl ketones as potential phospholipase A2 inhibitors", Journal of the Chemical Society, pp. 2271-2276 (2000).

Thommesen et al., "Selective Inhibitors of Cytosolic or Secretory Phospholipase A2 Block TNF-Induced Activation of Transcription Factor Nuclear Factor-Kappa B and Expression of ICAM-1", The Journal of Immunology, vol. 161, pp. 3421-3430 (1998).

Flock et al., "Synthesis of Some Polyunsaturated Sulfur- and Oxygen-containing Fatty Acids Related to Eicosapentaenoic and Docosahexaenoic Acids", Acta Chemica Scandinavica, vol. 53, pp. 436-445 (1999).

Andersen et al., "Elevated Expression of Human nonpancratic Phospholipase A2 in Psoriatic Tissue", Inflammation, vol. 18, No. 1 (1994).

Johansen et al., "Phospholipase A2 in Psoriasis", Uhl W. Nevalainen, Buchler MW (eds): Phospholipase A2 Basic and Clinical Aspects in Inflammatory Diseases, Prog. Surg. Basel, Karger, vol. 24, pp. 225-231 (1997).

Six et al., "The expanding superfamily of Phospholipase A2 enzymes: Classification and characterization" Biochmica et Biophysica Acta, pp. 1-19 (2000).

Anthonsen et al., "Functional Coupling between Secretory and Cytosolic Phospholipase A2 Modulates Tumor Necrosis Factor—a- and Interleukin-1B-induced NF-KB Activation", The Journal of Biological Chemistry, vol. 276, No. 32, pp. 30527-30536 (2001).

Sjursen et al., "Secretory and Cytosolic Phospholipase A2 Regulate the Long-Term Cytokine-Induced Eicosanoid Production in Human Keratinocytes", Cytokine, vol. 12, No. 8, pp. 1189-1194 (2000).

Sundler et al., "Acyl-chain selectivity of the 85 kDa Phospholipase A2 and the release process in intact macrophages", Biochem. J., pp. 455-458 (1994).

http://www.evelyscience.com/Chemistry/Glossary/E.php (accessed Jul. 9, 2008).

Miller et al., "Dietary Supplementation with Ethyl Ester Concentrates of Fish Oil (n-3) and Borage Oil (n-6) Polyunsaturated Fatty Acids Induces Epidermal Generation of Local Putative Anti-Inflammatory Meabolites", Journal of Investigative Dermatology, vol. 96, No. 1, pp. 98-103 (1991).

Aldamiz-Echevarria et al., "Effect of docosahexaenoic acid administration on plasma lipid profile and metabolic parameters of children with methylmalonic acidaemia", J Inherit Metab Dis, vol. 29, pp. 58-63 (2006).

http://www.webmd.com/skin-problems-and-treatments/psoriasis-overview (accessed Sep. 18, 2007).

Sandri et al., "Syntheses of all-(Z)-4, 7, 10, 13, 16, 19-Docosahexaenoic Acid from (Z)-1, 1, 6, 6-Tetralsopropoxy-2-hexene", J. Org. Chem., vol. 60, pp. 6627-6630 (1995).

USE OF POLYUNSATURATED KETONES FOR THE TREATMENT OF PSORIASIS

The present application is a continuation of U.S. application Ser. No. 12/713,917 as filed on Feb. 26, 2010, which application is a continuation of U.S. application Ser. No. 10/502,414 filed on Jan. 11, 2005 (now U.S. Pat. No. 7,687,543), which application is a U.S. National Stage of International Application No. PCT/GB03/00364, as filed on Jan. 29, 2003, which claims priority to GB0202002.2 as filed on Jan. 29, 2002. The entire contents of each of these applications are incorporated herein by reference.

This invention relates to the use of certain polyunsaturated long-chain ketones for the treatment of psoriasis and in particular to ketones carrying electron withdrawing substituents alpha to the carbonyl functionality in such treatment.

Psoriasis is a common, chronic, inflammatory skin disorder. Psoriatic tissue is characterised by chronic inflammation in both epidermis and dermis, the disease being further characterised by hyperplasia of epidermal keratinocytes, fibroblast activation, alteration of eicosanoid metabolism, and leukocyte infiltration.

Effective treatments for psoriasis such as cyclosporin A, steroids, methotrexate and photochemotherapy all have immunosuppressive activity and are thus not ideal treatments due to their side effects. Scientists have therefore pursued other potential treatments for this disease.

It has been observed that psoriatic tissue exhibits elevated levels of arachidonic acid and eicosanoids. This suggests that phospholipase $A_2$ ($PLA_2$) may be involved in the pathogenesis of psoriasis.

The phospholipases are a group of enzymes that release unsaturated fatty acids from the sn2 position of membrane phospholipids. Once released, the fatty acids are converted by various enzymes into biologically very important signalling molecules. Release of arachidonate initiates the arachidonate cascade leading to the synthesis of eicosanoids such as prostaglandins. Eicosanoids are important in a variety of physiological processes and play a central role in inflammation. In Inflammation, Vol. 18, No. 1 1994, Andersen et al identify the presence of certain phospholipases in psoriatic human skin.

It is therefore believed that inhibition of phospholipase enzymes should have potential in curing some of the inflammatory symptoms, including epidermal hyperproliferation due to increased leukotriene production, related to eicosanoid production and cell activation in both epidermis and dermis in psoriasis.

In J. Chem. Soc. Perkin Trans. 1, 2000, 2271-2276 several structurally different compounds are reported as inhibitors of $cPLA_2$ in vitro. The compounds tested were based around (all-Z)-eicosa-5,8,11,14,17-pentaenoic acid (EPA) and (all-Z)-docosa-4,7,10,13,16,19-hexaenoic acid (DHA). The paper suggests that preliminary studies show that in vitro the compounds are active as enzyme inhibitors.

The compounds in J. Chem. Soc. Perkin Trans. 1, 2000, 2271-2276 have however not been tested in vivo and there is thus no way of predicting their in vivo effects. In addition, when devising a treatment for a disease it is necessary to ensure selectivity. There are a very large number of phospholipase enzymes known and more enzymes of this type are being discovered as medical science develops. Since phospholipases control a wide variety of different intracellular functions it is necessary to develop inhibitors of these enzymes that are selective for the particular phospholipase whose activity is to be altered. Compounds which inhibit a large number of phospholipase enzymes are of little commercial interest since the benefits of a desired enzymic inhibition will be opposed by the presence of many unwanted and potentially dangerous side effects caused by unwanted enzyme inhibitions. There remains a need therefore, to provide highly selective inhibitors of phospholipase enzymes.

The present inventors have surprisingly found that compounds of somewhat similar structure or the same structure as those identified in the Perkin Transactions paper are selective for IVa PLA enzymes and are therefore ideal candidates for the treatment of psoriasis in the absence of side effects. Given that there are a total of 23 enzymes in the phospholipase group and each enzyme fulfils a different physiological and pathological function this is surprising. Moreover, the compounds of the invention have surprisingly been found to be particularly potent in reducing eicosanoid production, by for example, the inhibition of group IVa $PLA_2$.

Thus, viewed from one aspect the invention provides the use of a compound of formula (I)

$$R\text{---}CO\text{---}X \qquad (I)$$

(wherein R is a $C_{16\text{-}24}$ unsaturated hydrocarbon group optionally interrupted α, β, γ, or δ to the carbonyl group by a heteroatom or group of heteroatoms selected from S, O, N, SO, $SO_2$, said hydrocarbon group comprising at least 5 non-conjugated double bonds; and X is an electron withdrawing group) for the manufacture of a medicament for the treatment of psoriasis.

Viewed from another aspect the invention provides a method of treating psoriasis comprising administering to an animal, preferably a mammal, e.g. human, an effective amount of a compound of formula (I) as hereinbefore described.

Viewed from another aspect the invention provides use of a compound of formula (I) as hereinbefore described for use in the manufacture of a medicament for inhibiting the enzyme IVa $PLA_2$.

Viewed from yet another aspect, the invention provides a pharmaceutical composition comprising a compound of formula (I) as hereinbefore described.

The group R preferably comprises 5 to 7 double bonds, preferably 5 or 6 double bonds, e.g. 5 double bonds which should be non-conjugated. It is also preferred if the double bonds do not conjugate with the carbonyl functionality.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the carbonyl group which may be in the trans configuration.

The group R may have between 16 and 24 carbon atoms, preferably 19 to 21 carbon atoms.

The group R may carry a heteroatom or group of heteroatoms positioned α, β, γ, or δ to the carbonyl, preferably β or γ to the carbonyl. Preferably the heteroatom is O or S or a sulphur derivative such as SO.

Specifically preferred RCOX groups are those of formula

-continued

The R group may carry up to three substituents selected from halo or $C_{1-6}$-alkyl. If present the substituents are preferably non-polar, and small, e.g. a methyl group. It is preferred however, if the R group remains unsubstituted.

The group X is an electron withdrawing group. Suitable groups in this regard include O—$C_{1-6}$ alkyl, CN, $CO_2$—$C_{1-6}$ alkyl, phenyl, $CHal_3$, $CHal_2H$, $CHalH_2$ wherein Hal represents a halogen, e.g. fluorine, chlorine, bromine or iodine, preferably fluorine.

In a preferred embodiment the electron withdrawing group is $CHal_3$, especially $CF_3$.

Highly preferred compounds for use in the invention are $EPACOCF_3$, $EPASCOCF_3$ and AKH 217 as depicted below.

Compounds of formula (I) may be manufactured using known chemical synthetic routes. It is convenient to begin synthesis from the commercially available compounds arachidonic acid, EPA or DHA. Conversion of the acid functionality of these compounds into, for example a —$COCF_3$ group can be achieved readily, e.g. by converting the carboxylic acid into its corresponding acid chloride and reacting the same with trifluoroacetic anhydride in the presence of pyridine.

Introduction of a heteroatom into the carbon chain is also achieved readily. Conveniently, for example, the starting acid is reduced to an alcohol and, if required, converted to the corresponding thiol. The nucleophilic thiol may then be reacted with a group such as $BrCH_2COCF_3$ thereby introducing the carbonyl and electron withdrawing species. Complete synthetic protocols may be found in J. Chem. Soc., Perkin Trans 1, 2000, 2271-2276 or J. Immunol., 1998, 161, 3421.

The compounds of formula (I) may be formulated into medicaments using conventional techniques well known to the skilled pharmaceutical chemist. Thus, the compounds may be formulated with well known excipients or pharmaceutical carriers.

The medicaments of the invention may also comprise other conventional additives such as antioxidants, preservatives, colouring, flavouring etc.

The medicaments of the invention may be formulated as tablets, pills, powder, capsules, emulsions but are preferably in the form of creams or ointments. The mode of administration may be any known mode, such as oral, nasal, transmucosal, parenteral, topical, intradermal etc. However, it is advantageous if the medicament is applied topically, i.e. directly to the infected part of the human skin.

The amount of the medicament required to effect a successful treatment will, of course, depend on the patient and on the severity of the psoriasis. The dose will be readily determined by the skilled chemist.

The compounds of the invention may be used to treat psoriasis in combination with other known pharmaceuticals for said purpose and this forms a further aspect of the invention.

The invention is described further below with reference to the following non-limiting examples and figures.

MATERIALS AND METHODS

Materials

Calcium ionophore $A_{23187}$, Sigmacoat, 3-(4,5-dimethylthiazol-2-yl)-2,5-diphenyl tetrazolium bromide (MTT) and bovine serum albumin were obtained from Sigma (St. Louis, Mo., USA). Phosphatidylcholine, 1-stearoyl-2-arachidonyl and [3H] arachidonic are from Amersham (Buckinghamshire, UK). Aluminium sheets silica gel 60, ethyl acetate, iso-octane and acetic acid were purchased from Merck (Darmstadt, Germany). TNFα was a generous gift from Professor Terje Espevik, Norwegian University of Science and Technology, NTNU and IL-1β was purchased from Roche Molecular Biochemicals.

AACOCF₃ is from BIOMOL (Plymouth Meeting, Pa., USA), and MAFP is from Cayman (Ann Arbor, Mich., USA). All fatty acid compounds were stored under $N_2$ at $-80°$ C.

Cell Culture

The spontaneously immortalized human skin keratmocyte cell line HaCaT was kindly provided by Prof. N. E. Fusenig (Heidelberg, Germany). Cells were grown in Dulbecco's Modified Eagle's Medium (DMEM) with 1 g glucose/l (Gibco BRL, Life Technologies Ltd, Paisley, Scotland), supplemented with 5% fetal calf serum (FCS) (HyClone Laboratories, Inc., Utah, USA), 0.3 mg/ml L-glutamine (Sigma Chemical Company, St. Louis, Mo., USA), 0.1 mg/ml gentamicine (Sigma) and 1 μg/ml fungizone (Gibco). Confluent cells were stimulated with $A_{23187}$, Il-1β (10 mg/ml) or TNFα (10 mg/ml) in 0.5% (v/v) FCS for 1 hour before harvesting. Passages 40-80 of the cells were used. Generation of HaCat transfectants expressing luciferase under strict control of transcription factor NF-kB is described elsewhere (Anthonsen et al, J. Biol. Chem. 2001, 276, 30527). The reporter plasmid pBIIX contains two copies of the HIV NF-kB sequence cloned upstream of the mouse fos promoter driving expression of the *Photinus pyralis* luciferase gene.

EIA detection was performed according to manufacturer description, Cayman Chemical, Mich., USA. A dilution of 1:10 was used for $PGE_2$ measurement. Microplate Manager Software (Bio-Rad Laboratory) calculated sample data.

Luciferase Assay

Cells were seeded in 24-round multiwell plates ($2.8\times10^5$ cells/well). Treated cells were washed two times with phosphate-buffered saline and lysed, and luciferase activities were determined using the Luciferase Reporter Assay system (Promega) and Turner Luminometer model TD-20/20 (Turner Designs) as described by the manufacturer.

Synthesis of (all-Z)-Eicosa-5,8,11,14,17-Pentaenoic Acid (EPA) and (all-Z)-Docosa-4,7,10,13,16,19-Hexaenoic Acid (DHA) Derivatives The derivatives used in the enzyme assays are shown below. EPACOCF₃ was prepared as described in J. Immunol., 1998, 161, 3421. AACOCF3 and MAFP were bought from suppliers as mentioned above. The remaining derivatives were prepared as described in J. Chem. Soc. Perkin Trans. 1, 2000, 2271-2276.

Mixed-Micelle Assay of $cPLA_2$ Activity

Sources of IV $PLA_2$ enzyme activity were insect cells over expressing recombinant human IV $PLA_2$ (10 μg IV $PLA_2$ protein/$10^6$ cells; Bac PAK Baculovirus expression system; CLONTECH Laboratories, Palo Alto, Calif., USA). Cytosolic fractions of insect cells were prepared as described in Schalkwijk et al (1992) Eur. J. Biochem. 210, 169-176.

The protein contents of the cytosolic fractions were measured with Bio-Rad protein assay (Bio-Rad Laboratories GmbH, Munich, Germany) using bovine serum albumin as standard. The inhibitory derivatives were added 10 minutes prior to substrate addition. The preincubation of inhibitors was performed at room temperature. IV $PLA_2$ enzyme activity was analyzed using [14C]-L-3 Phosphatidylcholine, 1-stearoyl-2-arachidonyl as substrate according to Wijkander et. al. (Eur. J. Biochem. 202, 873-880, 1991). After 30 min the reaction was stopped and centrifuged, the $CHCl_3$ phase was evaporated with $N_2$ gas to dryness and then resuspended in $CHCl_3$:MeOH (9:1, v/v). Thin layer chromatography (TLC) separated free arachidonic acid from phospholipids on aluminum sheets silica gel 60 developed with ethyl acetate:isooctane:acetic acid:water (55:75:8:100, v/v/v/v) (Gronnich et al, J. Clin. Invest., 93, 1224-1233, 1994). Phosphor-Imager quantified free arachidonic acid and phospholipids, and IV $PLA_2$ activity was expressed as decreased arachidonic acid release by enzyme incubated with inhibitor compared to no inhibitor.

Arachidonic Acid and Eicosanoid Detection

Confluent cells were labelled with 1 μCi/ml [³H] arachidonic acid in media supplemented with 0.5% (v/v) FCS 24 hours before cell induction and inhibition. About 90% of the radioactive arachidonic acid were incorporated in the cell membranes. Extracellular [³H] arachidonic acid was removed by washing the cells 3 times in media. The HaCaT cells were then preincubated with inhibitor for 1 hour and stimulated with calcium ionophore for 1 hour. The cell media were collected and cleared by centrifugation. Arachidonic acid and eicosanoids were extracted from media using Bond Elut C18 octadecyl columns (500 mg) (Varian SPP, Harbor City, Calif.) as described by Powell, Anal. Biochem. 164, 117-131, 1987; with modifications previously described Brekke, Cytokine, 4, 269-280, 1992. The samples were collected in glass tubes precoated with Sigmacoat. The ethyl acetate solution of samples were completely dried with $N_2$, redissolved in 0.5 ml fresh ethyl acetate and aliquots of 50 µl (triplicates) samples were subjected to liquid β-scintillation counting (Beckman LS 1701) in 5 ml Ready Protein liquid (Beckman).

The amount of $PGE_2$ in cell culture media from calcium ionophore stimulated HaCaT cells was measured using an enzyme immunoassay (EIA; Cayman). The assay is based on the competition between free $PGE_2$ and a $PGE_2$-acetylcholinesterase for a limited amount of $PGE_2$ monoclonal antibody. The media were diluted 1:10 before analyzing of the $PGE_2$ contents. Microplate Manager Software (Bio-Rad Laboratory) calculated the sample data.

MTT Assay

Confluent cells were pretreated with inhibitors in serum free medium for 1 hour, and then treated with stimulating agent for 1 hour. Conversion of substrate [3-(4,5-dimethylthiazol-2-yl)-2,5-diphenyl tetrazolium bromide] was measured as optical density at 580 nm after 4 hours according to Mosmann [Mosmann T, J. Immunol. Methods 65, 55-63, 1983]. For each concentration of inhibitor nine parallels were measured.

Results

IV $PLA_2$ Enzyme Activity

Figure 1:
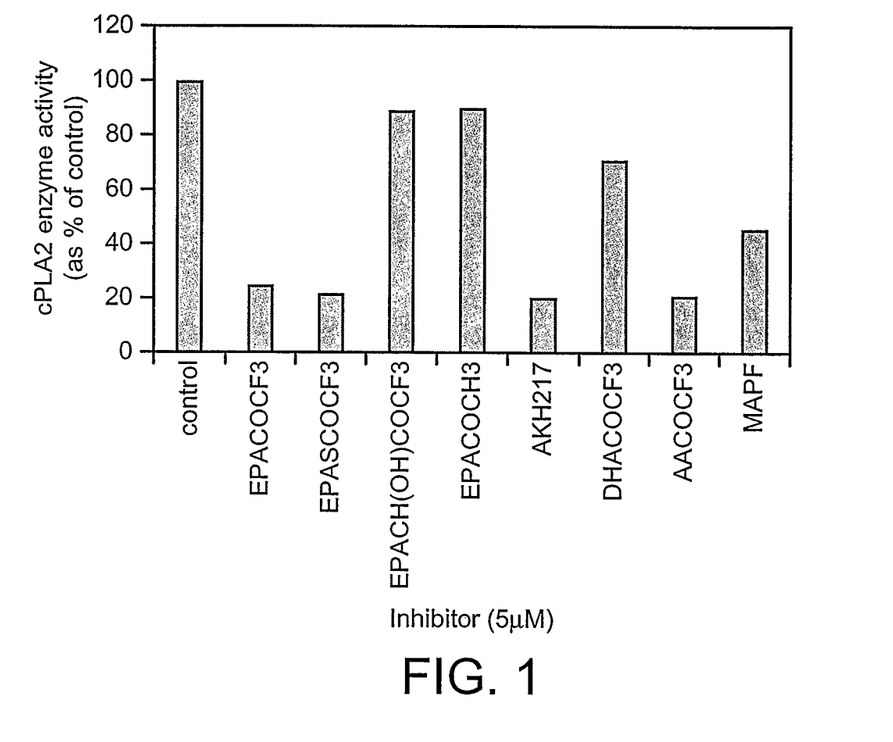
FIG. 1 shows the relative inhibition of IVa $PLA_2$ enzyme activity for a number of compounds of the invention in comparison to commercial compounds. Recombinant IVa $PLA_2$ enzyme was preincubated with inhibitor (5 μM) for 10 minutes and then assayed in the mixed-micelle enzyme activity assay. The control was not pretreated with inhibitor. Results are given as % of control and are mean of duplicate determinations from 1 out of 4 representative experiments.
Figure 2A:
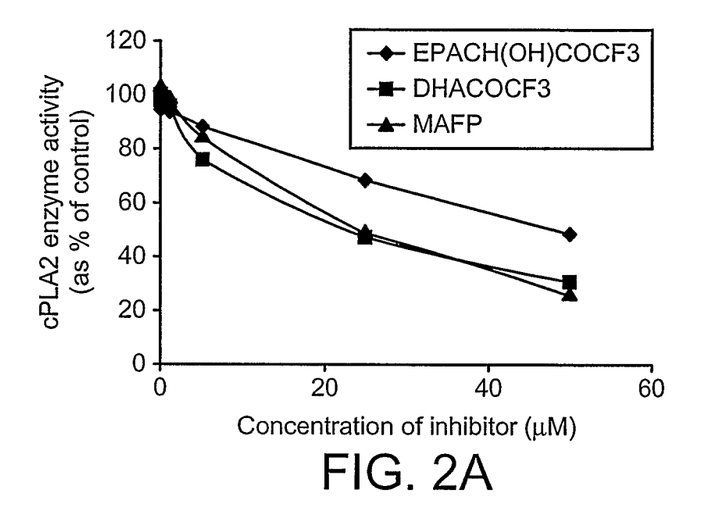
FIG. 2 shows concentration dependent inhibition of IVa $PLA_2$ in the mixed-micelle enzyme activity assay. Increasing inhibition of IVa $PLA_2$ by $EPACOCF_3$, $EPASCOCF_3$ and $AACOCF_3$ are shown in Figure B, and increasing inhibition of IVa $PLA_2$ by EPACH (OH) $COCF_3$, $DHACOCF_3$ and MAFP are shown in Figure A. Results are given as % of control and are mean of duplicate determinations from one out of 2 to 4 representative experiments.
Figure 2B:
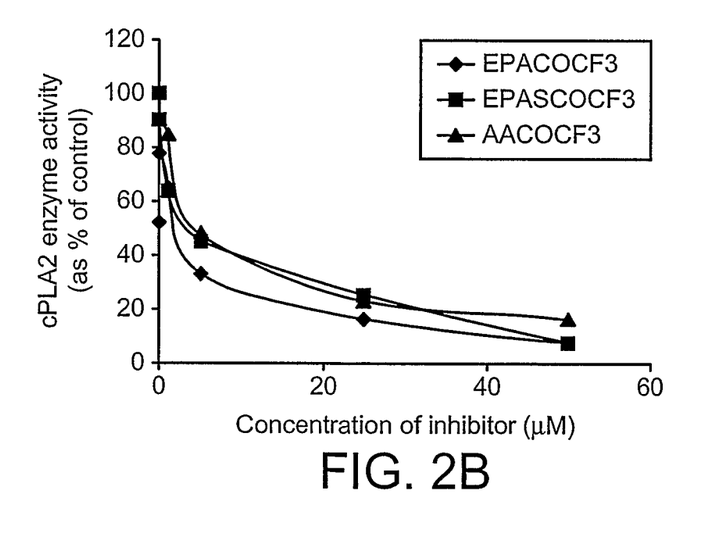

In order to investigate the action of the fatty acid derivatives as inhibitors of IV $PLA_2$, we measured the IV $PLA_2$ activity in the mixed micelle assay with recombinant IV $PLA_2$ as enzyme source, as described in materials and methods. The synthetic fatty acid derivatives we made are listed above, together with the commercial available inhibitors, which we used for comparison. $EPACOCF_3$, $EPASCOCF_3$ and AKH-217 seem to have the same potency as IV $PLA_2$ inhibitors as $AACOCF_3$ (i.e. 75-80% inhibition) (FIG. 1). MAFP and $DHACOCF_3$ were poorer IV $PLA_2$ inhibitors (50% and 30% inhibition respectively). The compound $EPACH(OH)CF_3$ was also tested which results in severe attenuation of inhibitory effect (10% inhibition). $EPACOCH_3$ was made as a control compound with methyl instead of the trifluoromethyl ($CF_3$) group. $EPACOCH_3$ showed no inhibition (FIG. 1). The $IC_{50}$ values of $EPACOCF_3$, $EPASCOCF_3$ and $AACOCF_3$ were measured to be 2.9±1.9, 3.5±0 µM and 5.8±1.9 µM respectively (FIG. 2B). While the $IC_{50}$ values of $DHACOCF_3$, MAFP and EPACH (OH) $CF_3$ were determined to be 21.3±1.5 µM, 24±1.4 µM and 43±7.1 µM respectively (FIG. 2A).

Kinetic studies with the inhibitors in the mixed micelle assay were performed in order to see if the time course was linear. A peak was achieved in two minutes (results not shown), indicating that the inhibitors are very fast acting.

In summary $EPACOCF_3$, $EPASCOCF_3$ and AKH217 seem to have similar or perhaps slightly higher potency as the commercially available compound $AACOCF_3$ in inhibiting IVa $PLA_2$.

Arachidonic Acid and Eicosanoid Detection

Figure 3A:
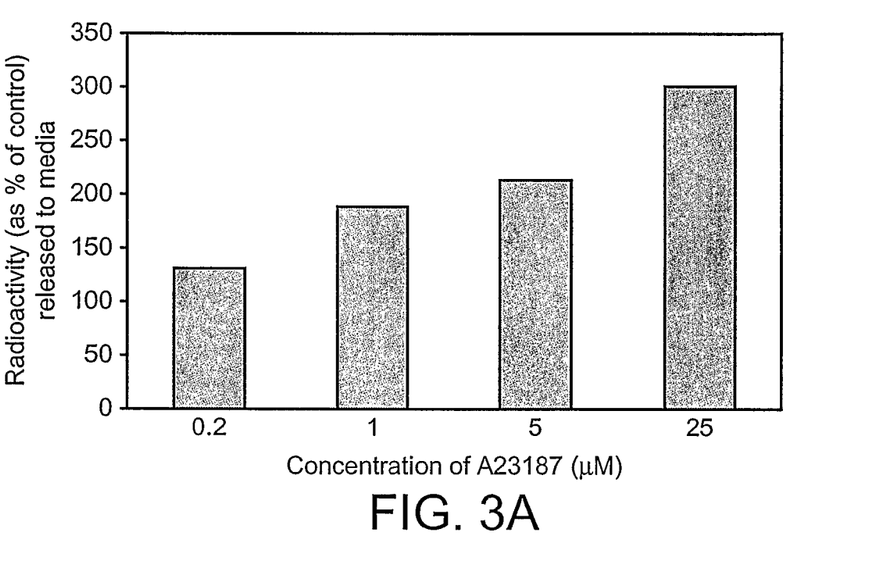
FIG. 3A shows that calcium ionophore $A_{23187}$ stimulates extracellular release of [3H]-labelled lipid in a concentration-dependent manner. HaCaT cells were treated with $A_{23187}$ for 1 hour, arachidonic acid and eicosanoids were extracted from cell media using Bond Elut C18 columns and contents of [3H]-labelled lipids in media were determined by scintillation counting. Each column in the figure represents the average of triplicate determinations from one out of 3 representative experiments.

In order to evaluate the effect of EPA and DHA derivatives in a more biological system, we utilized the HaCaT cells as a model system [Sjursen et al, Cytokine, 12, 8, 1189-1194, 2000]. The calcium ionophore $A_{23187}$ has been shown to induce arachidonic acid release in many cell types, probably by increasing the intracellular $Ca^{2+}$-concentration and thereby inducing the association of $cPLA_2$ with cellular membranes [Kramer and Sharp, FEBS Lett, 410, 49-53, 1997]. In HaCaT cell, the ionophore induced a dose response release of [3H]-labelled arachidonic acid (FIG. 3A).

Concentrations higher than 10 µM of $A_{23187}$ were toxic as determined by MTT assay.

The next step in evaluating our synthetic fatty acid inhibitors was to examine their ability to reduce the extracellular release of $PGE_2$ in response to $A_{23187}$ in HaCaT cells. Before the cell experiments were performed, we evaluated the toxicity of the inhibitors. MTT assay showed that concentrations of 25 µM and higher of the fatty acid compounds are toxic to HaCaT cells (results not shown).

Figure 3B:
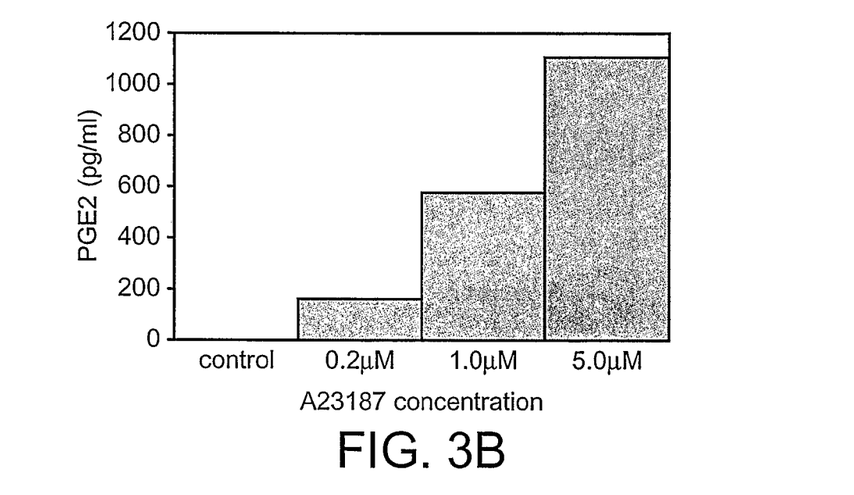
FIG. 3B shows that calcium ionophore $A_{23187}$ dosedependently also stimulates production of prostaglandin $E_2$ ($PGE_2$), a product of cyclooxygenase modification of arachidonic acid (AA). $PGE_2$ accumulation in medium was assayed by $PGE_2$ enzyme immunoassay (EIA).
Figure 4:
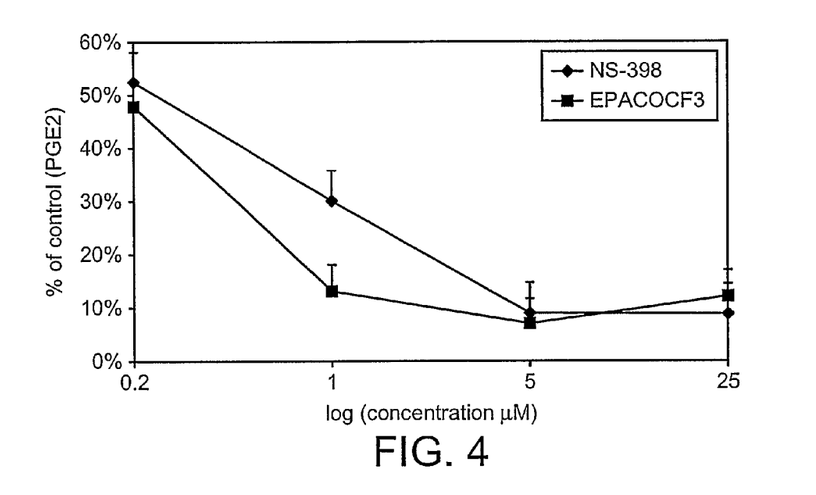
FIG. 4 shows that the fatty acid derivative $EPACOCF_3$ dosedependently is more powerful than the commercially available cyclooxygenase 2-selective inhibitor NS-398 in inhibiting $A_{23187}$-induced $PGE_2$ release in LPS-stimulated HaCat cells ($IC_{50}$ values 180 nM and 240 nM, respectively).

HaCat cells upregulate expression of cyclooxygenase 2 message when treated with LPS (200 ng/ml, 5% human serum) for 30 min. (unpublished results). Upon ionophore stimulation for one hour, $PGE_2$ accumulates in medium (FIG. 3B). The fatty acid derivative $EPACOCF_3$ was compared to NS-398, a cox-2 selective inhibitor, in its potency to reduce $PGE_2$ production by preventing release of its precursor AA. HaCat cells were pretreated with LPS (200 ng/ml, 5% human serum) for 30 min., treated with either inhibitors at different concentrations (0.2-25 µM) for another 30 min and stimulated with $A_{23187}$, 30 min. Finally, $PGE_2$ EIA was performed on cell media. The dose-response curve was constructed with respect to percent $PGE_2$ production without inhibitor. As can be observed in FIG. 4, $EPACOCF_3$ is much more potent than NS-398 in inhibiting $PGE_2$ production ($IC_{50}$ values of 180 nM and 240 nM, respectively), and indicates that substrate deprivation may be more powerful than activity inhibition for the cyclooxygenase.

Figure 5:
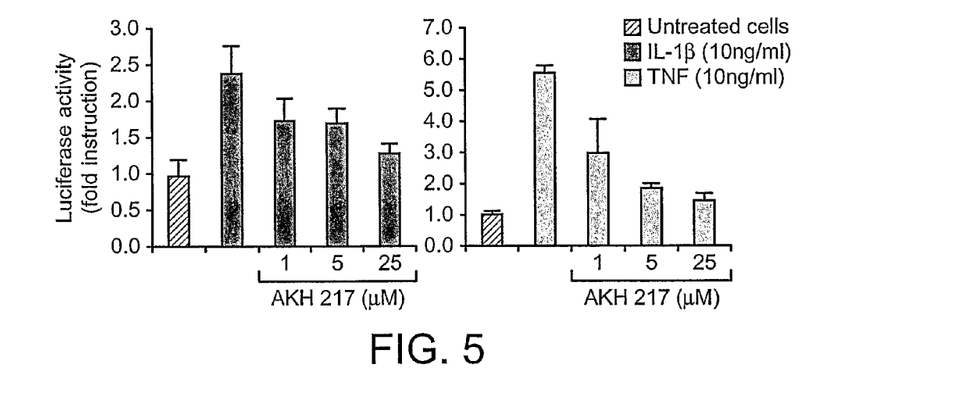
FIG. 5 shows that TNFα or IL-1β stimulated NF-kB activation is dose-dependently inhibited by AKH217 (91% and 81% respectively).

In order to determine if inhibition of IVa $PLA_2$ has any biologic consequence, HaCaT cells were stimulated with the proinflammatory cytokines IL-1β or TNFα. As a measure of inflammation, activation of the transcription factor NF-kB was analysed. We have shown earlier that TNFα or IL-1β activates NF-kB in HaCat cells (Thommesen et al, J. Immunol., 1998, 161, 3421). NF-kB activation was analysed as luciferase expression. Treatment of the stably transfected HaCat-pBIIX cells with TNFα or IL-1β for 1 h enhanced NF-kB-dependent expression (not shown). In the presence of inhibitors AKH217, IL-1β stimulated luciferase expression was dose-dependently inhibited by 81%. TNFα stimulated NF-kB activation was inhibited does-dependently AKH217 by 91% (FIG. 5) thus confirming that our synthetic fatty acid inhibitors may be useful in inhibiting inflammatory responses.

The invention claimed is:
1. A pharmaceutical composition comprising a compound of formula wherein the pharmaceutical composition is formulated for oral or nasal use.

2. The pharmaceutical composition of claim 1 wherein the pharmaceutical composition is further formulated as a pill, powder, capsule or emulsion.

3. A method of treating psoriasis comprising administering to a patient in need thereof the composition of claim 1.

4. A pharmaceutical composition comprising a compound of formula wherein the pharmaceutical composition is formulated for oral or nasal use; and further wherein the pharmaceutical composition further comprises an antioxidant, preservative, coloring additive or flavoring additive.

5. The pharmaceutical composition of claim 4 wherein the pharmaceutical composition is further formulated as a pill, powder, capsule or emulsion.

6. A method of treating psoriasis comprising administering to a patient in need thereof the composition of claim 4.

* * * * *